United States Patent [19]

Knips

[11] Patent Number: 4,490,552
[45] Date of Patent: Dec. 25, 1984

[54] PREPARATION OF ARYL ESTERS BY DECOMPOSING AN ARYL THALLIUM CARBOXYLATE

[75] Inventor: Ulrich Knips, Plettenberg, Fed. Rep. of Germany

[73] Assignee: Rutgerswerke AG, Fed. Rep. of Germany

[21] Appl. No.: 451,176

[22] Filed: Dec. 20, 1982

Related U.S. Application Data

[63] Continuation of Ser. No. 284,126, Jul. 16, 1981, abandoned, which is a continuation-in-part of Ser. No. 136,550, Apr. 2, 1980, abandoned, and Ser. No. 208,658, Nov. 20, 1980, abandoned.

[30] Foreign Application Priority Data

May 9, 1979 [DE] Fed. Rep. of Germany ....... 2918592
Dec. 11, 1979 [DE] Fed. Rep. of Germany ....... 2949671

[51] Int. Cl.³ .............................................. C07C 67/00
[52] U.S. Cl. ................. 560/130; 260/410.5; 546/268; 546/281; 546/301; 546/302; 549/66; 549/466; 549/470; 549/473; 549/484; 560/1; 560/22; 560/61; 560/62; 560/108; 560/109; 560/121; 560/122; 560/123; 560/124; 560/138; 560/139; 560/141
[58] Field of Search ............... 560/129, 139, 141, 122, 560/123, 124, 1, 20, 61, 62, 108, 109, 22, 121, 130, 138; 260/410.5, 347.5, 346.22; 546/285, 301, 322, 268, 281, 302; 549/66, 466, 470, 473, 484

[56] References Cited

U.S. PATENT DOCUMENTS 4,182,915 1/1980 Harvey ............................... 568/716

OTHER PUBLICATIONS

Kwok et al., J. Org. Chem., 44, 2309 (1979).
Taylor et al., JACS, 92, 2175 (1970).
Taylor et al., JACS, 93, 4845 (1971).

Primary Examiner—Nicky Chan
Attorney, Agent, or Firm—Charles A. Muserlian

[57] ABSTRACT

A novel process for the preparation of aryl esters of organic carboxylic acids in high isomer purity by decomposing a compound of the formula

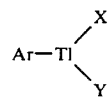

wherein Ar is an aryl radical, X is an acyloxy of an organic carboxylic acid and Y is selected from the group consisting of an acyloxy of an organic carboxylic acid and an anion of a strong organic and mineral acid in an aqueous media in the presence of a palladium salt or in the form of a two-phase reaction, wherein the aryl thallium salt is dissolved in water and the catalytic palladium salt is dissolved in a water-immiscible organic solvent and the reaction takes place with mixing.

15 Claims, No Drawings

PREPARATION OF ARYL ESTERS BY DECOMPOSING AN ARYL THALLIUM CARBOXYLATE

PRIOR APPLICATION

This application is a continuation of my U.S. patent application Ser. No. 284,126 filed July 16, 1981, now abandoned which in turn is a continuation-in-part application of my copending, commonly assigned U.S. patent applications Ser. No. 136,550 filed Apr. 2, 1980 and Ser. No. 208,658 filed Nov. 20, 1980, both now abandoned.

STATE OF THE ART

Aromatic hydrocarbons will react with thallium III salts to produce in high isomer purity arylthallium salts wherein the anion of the thallium salt may be of both of organic and inorganic acids. J.A.C.S., Vol. 92 (1970), p. 3520 describes the reaction of arylthallium bis-(trifluoroacetates) with lead tetraacetate which produces aryl trifluoroacetate esters as intermediates which were not isolated but the corresponding phenol was isolated. The process is not suitable for the production of aryl esters of organic carboxylic acids because of the large amounts of by-products produced.

Chem. Comm., 1971, p. 390 describes the reaction of palladium chloride (PdCl₂) with arylthallium salt type compounds using concentrated acetic acid as the solvent medium, but this process results in chlorinated aromatic compounds and predominately biphenyl compounds.

U.S. Pat. No. 4,182,915 describes a process for the preparation of nucleophilically ring-substituted aromatic compounds by reacting an aromatic thallium (III)-metallate with a source of the nucleophile. When this nucleophilic substituent is R—COO⁻ added as the carboxylic acid, the corresponding arylesters are formed. But since this reaction has to be run in an aqueous medium, water which is also a nucleophilic reagent is present and therefore the corresponding phenols also are formed. Besides the problems of separation of the pure arylesters, this side reaction lowers the yield. In addition, according to U.S. Pat. No. 4,182,915, phenol is formed when phenyldiacetate thallium is reacted in an aqueous medium without any other nucleophilic source.

OBJECTS OF THE INVENTION

It is an object of the invention to provide an improved process for the preparation of aryl esters of organic carboxylic acids in high isomer purity and high aryl ester yield.

This and other objects and advantages of the invention will become obvious from the following detailed description.

THE INVENTION

The novel process of the invention comprises decomposing a compound of the formula

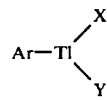

wherein Ar is an aryl radical, X is an acyloxy of an organic carboxylic acid and Y is selected from the group consisting of an acyloxy of an organic carboxylic acid and an anion of a strong organic and mineral acid in a neutral or acid aqueous media in the presence of a palladium salt soluble in the reaction medium to form the corresponding aryl ester of the organic carboxylic acid or in the form of a two-phase reaction wherein the arylthallium salt is dissolved in water or an aqueous solution and the catalytic palladium salt is dissolved in a water-immiscible solvent and the reaction takes place with mixing.

The aryl group may be mono- or polynuclear and may also be a heteroaryl group. Examples of suitable aryl groups are phenyl, tolyl, xylyl, naphthyl, anthracenyl, fluorenyl, phenanthrenyl, pyrenyl, n-propylphenyl, butylphenyls, ethylphenyl, cumenyl, p-cymenyl, alkoxyphenyls, halophenyls, biphenyls, pyridyls, carbonyloxyphenyls, aryloxyphenyls, thiophenes, benzofuranyls, etc.

Examples of suitable organic carboxylic acids of the salts are organic carboxylic acids of 1 to 18 carbon atoms wherein the acid may be an aliphatic, aromatic, cyclo-aliphatic or heterocyclic carboxylic acid. Examples of suitable acids are alkanoic acids such as formic acid, acetic acid, propionic acid, trifluoroacetic acid, butyric acid, isobutyric acid, valeric acid, isovaleric acid, trimethyl acetic acid, caproic acid, β-trimethyl propionic acid, heptanoic acid, caprylic acid, pelarginic acid, capric acid, undecylic acid, lauric acid, myristic acid, palmitic acid and stearic acid; cycloalkyl carboxylic acids such as cyclopentyl carboxylic acid, cyclopropyl carboxylic, cyclobutyl carboxylic acid and cyclohexyl carboxylic acid; cycloalkyl alkanoic acids, such as cyclopentyl acetic acid, cyclohexyl acetic acid, cyclopentyl propionic acid and cyclohexyl propionic acid; aryl carboxylic acids such as benzoic acid and 2,4-dinitrobenzoic acid; phenoxy alkanoic acids such as phenoxy acetic acid, p-chlorophenoxy acetic acid, 2,4-dichlorophenoxy acetic acid, 4-tert-butylphenoxy acetic acid, 3-phenoxy propionic acid and 4-phenoxy butyric acid; heterocyclic carboxylic acids such as furane-2-carboxylic acid, 5-tert-butylfurane-2-carboxylic acid; 5-bromofurane-2-carboxylic acid and nicotinic acids.

The anion of the strong organic or mineral acid may be derived from mineral acids such as nitric acid, perchloric acid and sulfuric acid and sulfonic acids such as perfluorobutane sulfonic acid herein after called nonaflonic acid.

Any monoaryl thallium salt which can be prepared by known methods may be used but the preferred salts are aryl thallium (III) perchlorate carboxylates since they are highly soluble in pure acid-free water without any significant hydrolysis or decomposition phenomena. Also useful is p-tolyl thallium acetate nonaflate.

If the desired carboxylic acid moiety of the aryl ester is not present as an anion in the monoarylthallium III salt starting material, it is preferred to react monoarylthallium bis-(trifluoroacetates) in portions with a dilute aqueous solution of the desired carboxylic acid, i.e. about 5% according to the following reaction.

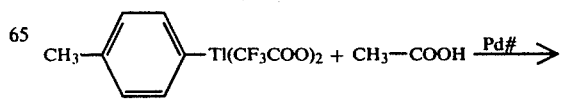

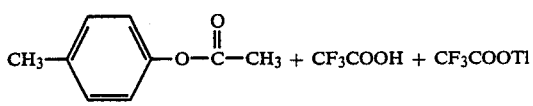

The carboxylic acid moiety in the thallium salt replaces the thallium moiety to form the aryl ester.

Among the preferred starting materials are the monoarylthallium salts containing the desired carboxylic acid moiety. The monoarylthallium dicarboxylates which are easily prepared are preferred and these are lower alkanoic acids such as propionic acid or isobutyric acid. For the preparation of acetic acid esters, it is preferred to use monoarylthallium acetate salts of strong acids such as perchloric acid or nonaflonic acid as they are more readily accessible than the diacetates and avoid the use of very expensive trifluoroacetic acid in the case of the bis-(trifluoroacetates) although these can be obtained in excellent yields and purity.

The palladium salt may be any salt soluble in the reaction medium and examples of suitable salts are palladium chloride ($PdCl_2$), palladium nitrate [$Pd(NO_3)_2$], palladium perchlorate [$Pd(ClO_4)_2$] and palladium acetate [$Pd(OOC-CH_3)_2$]. The said salts are used in catalytic amounts which may range from 0.5 to 5 mole % based on the arylthallium salt.

The reaction is preferably effected in water but an aqueous medium containing up to 50% by weight of an organic carboxylic acid may also be used. Concentrated acids such as more than 50% acetic acid reduce the yield of the desired aryl esters as the corresponding biaryls become the main product. The reaction is preferably effected at atmospheric pressure and under mild conditions such as temperatures of 20° to 100° C., preferably 40°–70° C., for 2 to 4 hours. It is surprising that in this decomposition reaction, no phenol is formed.

The desired aryl esters of the organic carboxylic acids may be recovered from the aqueous reaction medium by known procedures such as by extraction. Extraction with an aryl organic solvent equivalent to the aryl ester is preferred if its boiling point is not substantially higher than 100° C. Examples of other suitable organic solvents are cyclohexane or petroleum ether. The desired aryl esters may be recovered by distillation of the solvent or by crystallization.

When the process is run as a two-phase reaction, the arylthallium salt is dissolved in water and the palladium salt is dissolved in a water-immiscible organic solvent. The palladium compounds used in this instance are those which are particularly easily soluble in non-aqueous solvents, for instance palladium (II) salts of organic acids such as low molecular weight aromatic carboxylic acids, but preferably aliphatic carboxylic acids such as palladium (II) acetate as well as palladium salts of mineral acids provided they are sufficiently soluble in the non-aqueous solvent used.

The palladium salts must be present in a molar ratio of palladium to thallium of 1:200 to 1:400. Lower palladium concentration still results in the reaction, but the reaction time is greatly delayed.

Examples of suitable solvents for the palladium salts are aromatic hydrocarbons such as benzene, toluene, ethyl-benzene, cumene, o-xylene, m-xylene, p-xylene, mesitylene or mixtures of these substances and alkanes and cycloalkanes as long as the dissolving power suffices for the amounts of palladium salts required.

The process is carried out so that the aqueous solution of the aryl thallium salts and the catalyst solution are combined and thus reacted with each other which is preferably achieved by vigorous stirring of the two-phase mixture. The carboxylic esters formed and the biaryls obtained as a by-product are separated with the non-aqueous medium from which they can be obtained in pure form by known methods, preferably by crystallization or distillation.

The selectivity of the reaction of the arylthallium salts to carboxylate esters obtained by the process of the invention can attain practically the optimum value of 100%. Thus, for example when using 2,4- and 2,5-xylyl thallium acetate-perchlorate, the corresponding xylyl acetate is obtained with a selectivity of 98% after 3 hours of reaction time at a reaction rate of 93% and 98%, respectively, p-tolyl acetate can be obtained under similar conditions after a reaction time of 2 hours with a selectivity of 95% in a 99% reaction. The selectivity is impaired considerably by the presence of free carboxylic acids and to a lesser extent by free mineral acids.

The aryl esters of carboxylic acids produced by the process of the invention are known compounds and depending on the aryl group may be used as intermediates. Some are useful as fragrances in the perfume industry, especially p-tolyl acetate. The phenyl esters of acetic acid may be thermally treated to obtain the corresponding phenols and ketene. Furthermore, aryl esters are useful intermediates for chemical synthesis, i.e. the Fries reaction to form o- and p-hydroxyacetophenones.

In the following examples thare are described several preferred embodiments to illustrate the invention. However, it is to be understood that the invention is not intended to be limited to the specific embodiments.

EXAMPLE 1

1 g of p-tolylthallium-bis-(trifluoroacetate) was added in portions over one hour at 40° C. to a solution of 10 g of 5% by weight of acetic acid containing 0.003 g of palladium chloride and the mixture was stirred at 40° C. for 4 hours. The mixture was extracted with 4 g of toluene and the organic phase was dried and evaporated to dryness to obtain 0.17 g (75.1% yield) of a mixture consisting of 44.6% by weight of p-tolyl acetate and 55.4% by weight of 4,4'-dimethylbiphenyl.

EXAMPLE 2

A solution of 0.0025 g of palladium chloride in 2.5 g of water was added to a solution of 1 g of p-tolyl thallium acetate (perchlorate) in 10 g of water and the mixture was stirred at 60° C. for 2 hours and was extracted with toluene. The organic phase was dried and evaporated to dryness to obtain 0.216 g (74.0% yield) of a mixture of 86.1% of p-tolyl acetate and 13.9% of 4,4'-dimethylbiphenyl. The aqueous phase which contained unreacted starting material, thallium (I) perchlorate and catalyst could be recycled to the starting step.

EXAMPLE 3

1 g of toluene, 4.18 g of thallium III acetate and 3.49 g of nonaflonic acid were dissolved in 10 g of acetic acid and the solution was stirred at 70° C. for 24 hours and was then cooled. The mixture was filtered and the colorless crystalline product which was soluble in ether containing ethanol was crystallized from cyclohexane to obtain 4.44 g (62% yield) of pure p-tolylthallium acetate (nonaflate). Analysis: $C_{13}H_{10}F_9O_5STl$: molecular weight=653.56

|  | % C | % H | % F | % S | % Tl |
|---|---|---|---|---|---|
| Calculated: | 23.89 | 1.54 | 26.16 | 4.90 | 31.27 |
| Found: | 23.54 | 1.71 | 25.82 | 5.01 | 31.00 |

1 g of the said p-tolylthallium acetate (nonaflate) was added in portions over 30 minutes to 10 g of water containing 0.002 g of palladium for 4 hours. The mixture was extracted with 4 g of toluene and the organic phase was dried and evaporated to dryness to obtain 0.146 g (71.4% yield) of a mixture of 80.8% of p-tolyl acetate and 19.2% of 4,4-dimethyl biphenyl. The aqueous phase containing catalyst, unreacted starting material and thallium I nonaflate was recycled for the next reaction.

EXAMPLE 4

A solution of 1000 parts by weight of p-tolyl thallium acetate perchlorate (p-CH$_3$C$_6$H$_4$TlClO$_4$CH$_3$COO) in 6000 parts by weight of water and a solution of 2 parts by weight of palladium (II)-acetate [Pd(OAc)$_2$] in 1500 parts by weight of benzene were stirred together vigorously for 2 hours at 60° C. Then the organic phase was separated and the benzene was distilled off under reduced pressure. 310 parts by weight of a residue remained which contained 297 parts by weight of p-tolyl acetate and 11 parts by weight of 4,4-dimethyl biphenyl in addition to palladium compounds. The reaction rate was 99% with a selectivity of 95%. The mixture was rectified over a short column at 10 m bar with the fraction passing over between 79° and 85° C. consisting of pure p-tolyl acetate. The distillation residue was taken up in acetone, and 4,4'-dimethyl biphenyl in pure form was obtained by addition of water.

EXAMPLES 5 TO 7

1000 parts by weight of xylyl thallium acetate perchlorate were dissolved in 6000 parts by weight of water and the mixture was stirred vigorously for 3 hours with a solution of 2 parts by weight of Pd(OAc)$_2$ in 1500 parts by weight of benzen. The organic phase was separated and was distilled to dryness and the residue was rectified under reduced pressure to obtain the acetic aryl ester. The corresponding symmetrical tetramethyl biphenyl was obtained in pure form from the distillation residue after dissolution in acetone and precipitation with water. The results are reported in Table I.

TABLE I

| Example | xylyl radical | xylyl acetate parts by weight | tetramethyl biphenyl parts weight | reaction after 3 h % | selectivity % |
|---|---|---|---|---|---|
| 5 | 3,4— | 236 | 26 | 82 | 85 |
| 6 | 2,4— | 307 | 4 | 91 | 98 |
| 7 | 2,5— | 324 | 4 | 98 | 98 |

EXAMPLE 8

1000 parts by weight of p-ethyl-phenyl thallium acetate perchlorate were reacted by the procedure of Example 1 and after a reaction time of 2 hours, 291 parts by weight of a mixture were obtained which consisted of 276 parts by weight of p-ethyl-phenyl acetate and 15 parts by weight of 4,4'-dimethylbiphenyl. With a reaction rate of 89%, the selectivity of the ester formation was 92%.

EXAMPLE 9

(Comparative Example)

10 gm (21.2 mmoles) of p-tolyl thallium acetate perchlorate hydrate were dissolved in 100 gm of water and 4.23 gm (21.2 mmoles) of copper II acetate hydrate were added. The mixture was stirred for 5 hours at 60° C. and was extracted with benzene. The organic phase was analyzed by gas chromatography and neither p-tolyl acetate nor p-cresol could be detected.

EXAMPLE 10

(Comparative Example)

A mixture of 10 gm (21.2 mmoles) of p-tolyl thallium acetate perchlorate hydrate, 3.07 gm (21.2 mmoles) of ammonium iodide and 3.76 gm (21.2 mmoles) of palladium II chloride in 100 gm of water was stirred vigorously for 5 hours at 60° C. Seconds after starting the reaction, an intensive smell of p-iodotoluene appeared which was the only reaction product in about quantitative yield. Neither p-cresol nor p-tolylacetate could be detected.

Various modifications of the process of the invention may be made without departing from the spirit or scope thereof and it is to be understood that the invention is intended to be limited only as defined in the appended claims.

The comparative examples (examples 9 and 10) show that the U.S. Pat. No. 4,182,915 is not relevant to this new process. As example 9 demonstrates, the aryl thallium salts of the invention are not decomposed by a typical catalyst mentioned in U.S. Pat. No. 4,182,915.

Example 10 demonstrates that the addition of an iodide salt, which is the preferred method according to U.S. Pat. No. 4,182,915, to the aryl thallium salts of the invention will lead to the corresponding iodoaryl compound even in the presence of a palladium salt as catalyst.

This means the reaction of the invention should be conducted in the absence of an iodide salt.

I claimed:

1. A process for the preparation of an aryl ester of an organic carboxylic acid comprising decomposing a compound of the formula

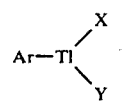

wherein Ar is an aryl radical, X is an acyloxy of an organic carboxylic acid and Y is selected from the group consisting of an acyloxy of an organic carboxylic acid and an anion of a strong organic sulfonic and mineral acid in a neutral or acidic aqueous medium at 20° to 100° C. for 2 to 4 hours at atmospheric pressure in the presence of a soluble palladium salt in a molar ratio of palladium to thallium of 1:200 to 1:400 and in the absence of an iodide salt.

2. The process of claim 1 wherein the aqueous medium is water.

3. The process of claim 1 wherein the aqueous medium is water containing up to 50% by weight of an organic carboxylic acid.

4. The process of claim 1 wherein the aryl thallium salt has the formula

Ar—Tl(CF$_3$—COO)$_2$.

5. The process of claim 1 wherein Y is CF$_3$—CF$_2$—CF$_2$—CF$_2$—SO$_3{}^-$.

6. The process of claim 1 wherein Y is ClO$_4$.

7. The process of claim 1 wherein the reaction is effected at 40° to 70° C. at atmospheric pressure.

8. The process of claim 1 wherein X and Y are both CH$_3$—COO$^-$.

9. The process of claim 1 wherein an aqueous solution of the aryl thallium compound and a solution of the palladium salt in a water-immiscible organic solvent are vigorously mixed together to obtain the formed aryl esters in the organic solvent and recovering the esters by distillation and/or crystallization.

10. The process of claim 9 wherein the aryl thallium salts are dissolved in pure water.

11. The process of claim 9 wherein the aryl thallium salts are dissolved in an aqueous solution of up to 50% by weight of a water soluble carboxylic acid.

12. The process of claim 9 wherein the aryl thallium salt has the formula

Ar—Tl—(CF$_3$—COO)$_2$.

13. The process of claim 9 wherein the aryl thallium salt has the formula

Ar—TlX ClO$_4$.

14. The process of claim 9 wherein the aryl thallium salt has the formula

AR—TlX C$_4$F$_9$SO$_3$.

15. The process of claim 9 wherein the reaction is carried out at 40°–70° C. at atmospheric pressure for 2 to 4 hours.

* * * * *